United States Patent [19]

Fu et al.

[11] Patent Number: 5,843,786

[45] Date of Patent: Dec. 1, 1998

[54] ANALYSIS OF CARBOHYDRATES IN BIOLOGICAL FLUIDS BY HIGH PERFORMANCE LIQUID CHROMATOGRAPHY

[75] Inventors: Daotian Fu, Horsham; Ming He, Roslyn; David Zopf, Strafford, all of Pa.

[73] Assignee: Neose Technologies, Inc., Horsham, Pa.

[21] Appl. No.: 563,822

[22] Filed: Nov. 28, 1995

[51] Int. Cl.$^6$ ..................................................... G01N 30/02
[52] U.S. Cl. ........................... 436/94; 436/161; 436/177; 436/178
[58] Field of Search ............................. 436/94, 161, 177, 436/178, 164

[56] References Cited

U.S. PATENT DOCUMENTS 5,142,031  8/1992  Lee et al. .................................. 436/87

OTHER PUBLICATIONS

Ackerman, "The use of carbohydrates as therapeutic agents", Proceed. Intern. Symp. Control. Rel. Bioact. Mater., 20 (1993), Controlled Release Society Inc., pp. 148–149.
Lemonnier et al., "Low–molecular–weight carbohydrate–rich compounds in pregnancy urine", Biomedicine, 24 (1976) pp. 253–258.
Maury et al., "Relationship between urinary sialylated saccharides . . . ", Annals of the Rheumatic Diseases, 41 (1982) pp. 268–271.
Maury et al., "Urinary excretion of sialic acid–containg saccharides . . . ", Arthrits and Rheumatism, vol. 24, No. 9 (Sep. 1981) pp. 1137–1141.
Huttunen et al., "Increased urinary excretion of neuraminic acid–containing oligosaccharides . . . ", J. of Molecular and Cellular Cardiology, 4 (1972) pp. 59–70.

Witczak, "Carbohydrates as drugs and potential therapeutics", Current Medicinal Chemistry, 1 (1995) pp. 392–405.
Strydom, "Chromatographic separation of 1–phenyl–3–methyl–5–pyrazolone–derivatized neutral, acidic and basic aldoses", J. Chromatography 678 (1994) pp. 17–23.
Ui et al., "Purification of hog thyroglobulin", J. Biochem., vol. 50, No. 6 (1961) pp. 508–518.
Tettamanti et al., "Purification and charcaterization of bovine and ovine submaxillary mucins", Archives of biochemistry and biophysics, 124 (1968) pp. 41–50.
Fu et al., "Monosaccharide composition analysis . . . ", Anal. Biochem., 227 (1995) pp. 377–384.
Honda et al., "High–performance liquid chromatography of reducing carbohydrates . . . ", Anal. Biochem., 180 (1989) pp. 351–357.
The Merck Index, Tenth Edition (Windholtz, et al., eds.), Merck & Co, Inc (1983) p. 56.
Kuraya et al., 1992, *J. Biochem.* 112:122–126.
Kakehi et al., 1989, "Analysis of Carbohydrates by GLC and MS" (Biermann, C.J., and McGinniss, G.D., Eds.), pp.43–86.
Hardy et al., 1988, *Anal. Biochem.* 170:54–62.
Hase et al., 1978, *Biochem. Biophys. Res. Commun.* 85:257–263.
Smith et al., 1978, "Methods in Enzymology" (Ginsburg, V., Ed.), vol. 50, pp. 221–226.
Laine et al., 1972, "Methods in Enzymology" (Ginsburg, V., Ed.), vol.28, pp. 159–167.

*Primary Examiner*—Jan Ludlow
*Attorney, Agent, or Firm*—Pennie & Edmonds LLP

[57] ABSTRACT

The present invention is directed to a method of detecting reducing carbohydrates in a complex biological sample. The sample is filtered, subjected to ion exchange chromatography, derivatized, extracted and analyzed by HPLC.

10 Claims, 1 Drawing Sheet

ANALYSIS OF CARBOHYDRATES IN BIOLOGICAL FLUIDS BY HIGH PERFORMANCE LIQUID CHROMATOGRAPHY

BACKGROUND OF THE INVENTION

1. Field of the Invention

A simple and sensitive high performance liquid chromatography (HPLC)-based method for the analysis of monosaccharides and saccharide compounds in biological fluids is discussed.

2. Discussion of the Background

Reducing carbohydrates, (i.e. monosaccharide and oligosaccharides), are a class of compounds which have been identified as being present in biological samples. In particular, sialylated oligosaccharides, have been described in complex biological fluids such as human milk, blood and urine. Due to the complexity of biological fluids, a simple technique for analyzing for the presence of reducing carbohydrates, and in particular sialylated oligosaccharides, has been difficult to develop.

In the past, analysis of reducing carbohydrates has relied to a large extent on gas liquid chromatographic separation of trimethylsilyl, alditol acetate, and partially methylated alditol acetate derivatives. These methods require sample clean-up prior to derivitization and can be destructive to oligosaccharides, resulting in partial loss of structural information. Further, they required a relatively large amount of purified reducing carbohydrates, which practically limited their usefulness for analysis of minor amounts of reducing carbohydrates in biological fluids. (for example see Laine, R. A., et al in Methods in Enzymology (Ginsburg, V., edition), 1972, Vol. 28, pp. 159–167 and Kakehi, K., et al in Analysis of Carbohydrates by GLC and MS (Biermann, C. J., and McGinniss, G. D., Eds), 1989, pp. 43–86).

There have been numerous high performance liquid chromatography based methods with precolumn derivatizations. They all require tedious derivatization chemistry, and HPLC analysis can be interfered with by the presence of the large amount of contaminants in biological fluids. They also can degrade or modify analytes leading to partial loss of structural information. The most widely used method using 2-aminopyridine was reported by Hase, S. et al (1978, Biochem. Biophys. Res. Commun., 85, 257–263; 1992, J. Biochem., 112, 122–126). Unfortunately, the derivatization chemistry employed causes partial desialylation of the sialylated oligosaccharides and analysis of the derivatized oligosaccharides can be severely compromised by interfering contaminants in biological samples.

Recently, high pH anion-exchange chromatography with pulsed amperometric detection has been used for analysis of carbohydrates (Hardy, J. R., Townsend, R. R., and Lee, Y. C., 1988, Anal. Biochem., 170, 54–62). However, the electrochemical detection requires highly purified samples and many contaminants commonly present in biological samples, such as proteins and lipids, can interfere with carbohydrate analysis.

Honda et al. Analytical Biochem, 180, 351–357 (1989) reports a method for analyzing reducing carbohydrates obtained by hydrolysis of glycoproteins, by derivatization with 1-phenyl-3-methyl-5-pyrazolinone derivatives followed by HPLC. The method requires the use of acidic hydrolysis conditions inappropriate for qualitative analysis of sialyloligosaccharides. In addition, this method is inappropriate for analyzing complex biological fluids.

Fu et al. Analytical Biochem., 227, 377–384 (1995) reports a method for analyzing reducing carbohydrates, including sialic acids, obtained by hydrolysis of glycoproteins, by derivatization with 1-phenyl-3-methyl-5-pyrazolinone derivatives followed by HPLC. The method provides for quantitative analysis for sialic acids by hydrolysis from a glycoprotein or oligosaccharide with a neuraminidase or mild acid, followed by conversion to the corresponding mannosamine derivative with neuraminic acid aldolase. This method is able to quantify the amount of sialic acid in the original sample, but due to the hydrolysis conditions, qualitative information as to the source of the sialic acid is lost. In addition, this method is inappropriate for analyzing complex biological fluids.

The ability to qualitatively and quantitatively measure the levels of oligosaccharides in complex biological fluids, and in particular to monitor variations in the levels of specific sialyl oligosaccharides, has become important, because of the known correlation between the rate of urinary excretion of sialylated oligosaccharides and the clinical symptoms of rheumatoid arthritis (Maury et al, Annals of Rheumatic Diseases, 41, pp 268–271 (1982)), Systemic Lupus erythematosus (Maury et al Arthritis and Rheumatism, 24, pp 1137–1141 (1981)), myocardial infarction (Huttunen et al J. Molecular and Cellular Cardiology, 4, pp 59–70 (1972)) and pregnancy (Lemonnier et al Biomedicine, 24, pp 253–258 (1976)). In monitoring a disease state, it is important to be able to distinguish between different positional isomers of saccharide compounds (qualitative analysis), and in particular to differentiate between 3'sialyllactose and 6'sialyllactose. Accordingly, a simple yet sensitive method for quantitatively and qualitatively measuring the amount of reducing saccharide compounds in a complex biological fluid would be desirable.

SUMMARY OF THE INVENTION

Accordingly, one embodiment of the present invention is directed to a method for the analysis of reducing saccharide compounds from complex biological fluids. The present method is accomplished by i) filtering a biological fluid through a membrane or filtration device;

ii) separating charged from neutral saccharide compounds by contacting the filtered biological fluid with an anion exchange medium;

iii) derivatizing saccharide compounds in a filtrate with a 3-alkyl-5-pyrazolinone derivative of the formula

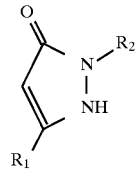

where $R_1$ is a $C_{1-12}$, preferably $C_{1-8}$ alkyl group; and
$R_2$ is a $C_{1-12}$ alkyl group, a substituted $C_{1-12}$ alkyl group, wherein said substitutions are $C_{1-8}$ alkyl, $C_{1-8}$ alkoxy or halogen, or a chromophore selected from the group consisting of phenyl, naphthyl, benzyl and pyridyl optionally substituted with $C_{1-8}$ alkyl, $C_{1-8}$ alkoxy or halogen; and iv) analyzing the derivatized filtrate by reverse-phase HPLC.

According to a second embodiment of this invention is a method of monitoring a disease state by analyzing the state of saccharide compound concentrations of a biological fluid.

Applicants have discovered that this simple method allows for the qualitative and quantitative analysis of saccharide compounds from a complex biological fluid.

DETAILED DESCRIPTION OF THE PREFERRED EMBODIMENTS

Figure 1:
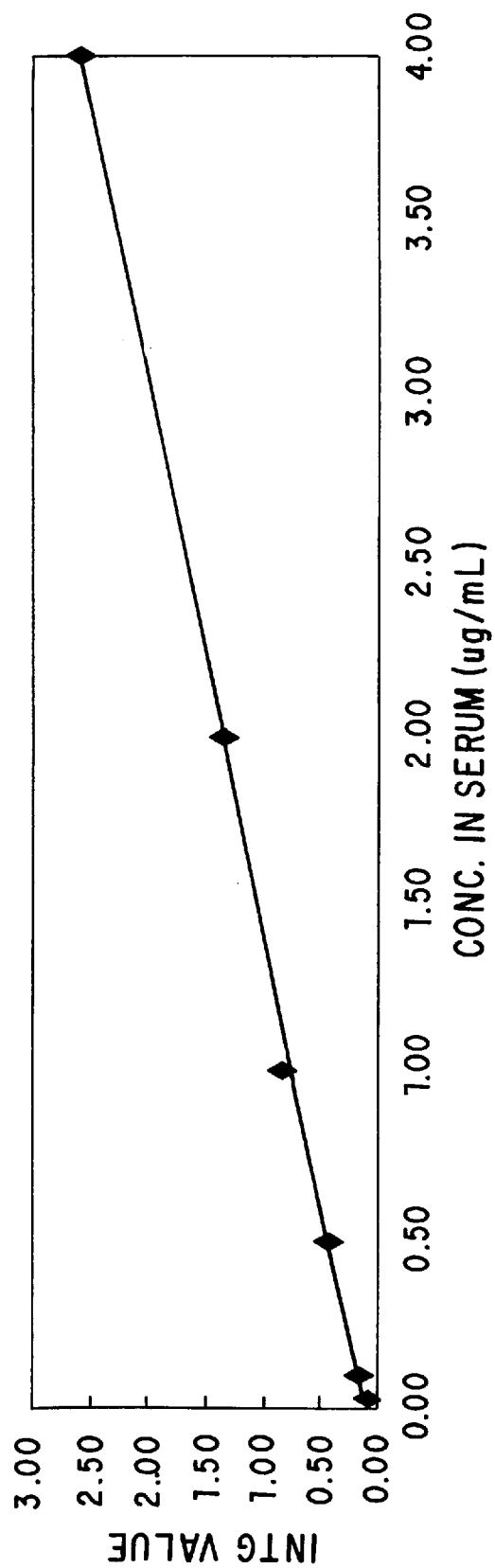
FIG. 1: Standard Curve of 3'-SL Analysis in Serum (with 6'-SL as internal standard).

Within the scope of the present invention the term "saccharide compound(s)" is used, to refer to reducing monosaccharide and oligosaccharide compounds. The mono and oligosaccharide compounds may be sialylated, phosphorylated or sulphated. Of particular interest are the oligosaccharide compounds 3'sialyllactose, 6'sialyllactose, 3'sialyllactosamine and 6'sialyllactosamine.

Almost any complex biological fluid which contains reducing saccharide compounds may by analyzed by the present method. Non-limiting examples of suitable fluids are whole blood, blood plasma, serous effusions, cerebral spinal fluid, saliva, milk, tears, sweat, pancreatic juice, gastric juice, sputum, pus, aqueous and vitreous humors from the eye, joint fluids and urine. Whole blood, plasma and urine are especially suitable for analysis.

The amount of saccharide compound found in a biological sample is typically very small, on the order of only $\leq 1$ $\mu$g per mL of biological fluid. However, the sensitivity of this analysis technique allows for the detection of even trace amounts of reducing saccharide compound, present in a concentration on the order of as little as 0.002 nanomoles/mL of fluid. Typically only 0.5–5 mL of biological fluid is needed to be analyzed.

In order to provide a simple and sensitive method for analyzing for saccharide compounds, the sample should be treated to remove contaminants which could interfere with the analysis. Such treatment will be dependent on the type of sample to be analyzed, and the type of contaminants present. For example, whole cells can be removed by simple filtration or centrifugation. Such a treatment will probably be unnecessary when the sample to be analyzed is blood plasma or urine.

After whole cells are removed, the sample should be treated to remove large molecules, by filtration through a filter with a 10,000–50,000 Mw cut-off, preferably a 10,000 Mw cut-off. The presence of high molecular weight proteins, lipids, glycoproteins and glycolipids could interfere with subsequent derivatization chemistry and possibly introduce free reducing oligosaccharides, via hydrolysis of a glycoprotein or glycolipid. Suitable filters, such as membranes, microdialysis membranes, hollow fiber devices, which separate based on molecular size are conventionally known to those of ordinary skill in the art. A suitable filter is the ULTRAFREE-MC filter cartridge available from Millipore Co.

The sample to be analyzed is then treated with an anion exchange medium to separate charged from neutral saccharide compounds. Because the analysis technique uses reverse phase HPLC methods, the presence of both charged and neutral saccharide compounds could possibly complicate the analysis due to insufficient resolution between two compounds. Accordingly, by separating the neutral saccharide compounds from the charged species, optimum resolution of the analysis technique is obtained. By passing the sample through an anion exchange medium, charged carbohydrates such as sialylated, sulfated and phosphorylated saccharide compounds are retained on the resin, while neutral carbohydrates will be recovered in the flow through fraction. In addition to simplifying the analysis by separating charged from neutral saccharide compounds, treatment with an anion exchange medium can provide for concentration of the charged saccharide compounds from the biological fluid, thus greatly increasing the sensitivity of the analysis method.

Methods for separating charged from neutral saccharide compounds are conventionally known to those of ordinary skill in the art. For example, a suitable separation technique is described by Smith et al in Methods in Enzymology (Ginsburg, V., Ed.), 1978, Vol. 50, pp. 221–226.

Suitable anion exchange media are conventionally known to those of ordinary skill in the art. A suitable anion exchange resin is Dowex 1-X8 which has been pre-treated sequentially with water, methanol, water and 1M acetic acid.

After the neutral saccharide compounds have been eluted from the anion exchange medium, with a solvent such as water, the charged saccharide compounds can be eluted from the anion exchange medium with a suitable buffer solution, such as 0.5M pyridine acetate buffer at pH 5.0. Suitable techniques for removing charged saccharide compounds are conventionally known to those of ordinary skill in the art. For example charged saccharide compounds can be removed with a suitable aqueous buffer solution, typically at 0.5 to 1.0M, at a pH of from 3 to 7, preferably from 4 to 6, most preferably about 5. In a preferred embodiment a volatile buffer such as pyridine acetate, ammonium acetate or triethylamine acetate are used.

In this fashion separate samples of neutral and charged saccharide compounds may be obtained and separately analyzed. The separate eluents may then be dried to remove water. If a volatile buffer is used, the buffer is also removed in this drying step. Almost any drying technique can be used to remove the water, so long as such drying does not degrade the saccharide compounds or result in lose of sample. Evaporation of the water at reduced pressure using vacuum centrifuge techniques is preferred.

After the complex biological sample has been filtered and subjected to the anion exchange medium, the separate fractions containing the charged and the neutral saccharide compounds can be subjected to derivatization with a 3-alkyl-5-pyrazolinone derivative.

The 3-alkyl-5-pyrazolinone derivative is of the formula

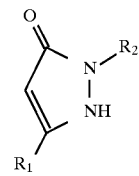

where $R_1$ is a $C_{1-12}$, preferably $C_{1-8}$ alkyl group; and $R_2$ is a $C_{1-12}$ alkyl group, a substituted $C_{1-12}$ alkyl group, wherein said substitutions are $C_{1-8}$ alkyl, $C_{1-8}$ alkoxy or halogen, or a chromophore selected from the group consisting of phenyl, naphthyl, benzyl and pyridyl optionally substituted with $C_{1-8}$ alkyl, $C_{1-8}$ alkoxy or halogen.

Suitable chromophore groups $R_2$ are preferably phenyl and substituted phenyl. Preferred phenyl substituents are H, $C_{1-8}$ alkyl, $C_{1-8}$ alkoxy, and halogens such as F, Cl, Br, and I. Most preferably the chromophore group is phenyl.

An especially suitable 3-alkyl 5-pyrazolinone derivative is 3-methyl 1-phenyl-2-pyrazolin-5-one (PMP) available from the Sigma Chemical Company.

Derivatization is generally conducted by adding a solution of the 3-alkyl-5-pyrazolinone derivative, such as PMP, to the sample to be derivatized, under basic conditions.

Suitable solvents are methanol, ethanol, dimethylsulfoxide and acetonitrile. Methanol and ethanol are preferred, with methanol being most preferred.

Suitable bases are sodium hydroxide, potassium hydroxide, lithium hydroxide, or metal alkoxide bases such as sodium methoxide, lithium ethoxide, sodium isopropoxide and potassium t-butoxide or metal hydride bases such as lithium hydride or sodium hydride.

Suitable reaction conditions are a temperature of 30 to 90, preferably from 60 to 80, most preferably about 70° C., at a pH of 7 to 10.

The sample to be derivatized is treated with enough 3-alkyl-5-pyrazolinone derivative to ensure that the reducing end of the saccharide compound is reacted with two 3-alkyl-5-pyrazolinone derivatives. Since the amount of saccharide compound is not yet known at this point of the analysis, the sample is typically treated with excess 3-alkyl-5-pyrazolinone derivative, typically at a 50 to $5 \times 10^7$ molar excess. Generally a biological sample is prepared to produce a sample to be derivatized containing from 1 picomole to 1 $\mu$mol of reducing saccharide compound. An estimate of the amount of saccharide compound present (sialylated or non-sialylated) can generally be determined by routine calorimetric analysis methods known to those of ordinary skill in the art. In general a sample containing 1 picomole to 1 $\mu$mol of reducing saccharide compound, in 60 $\mu$L of water, is treated with a solution containing about 37.5 $\mu$mole of 3-alkyl-5-pyrazolinone derivative.

A suitable procedure for conducting such a derivatization is described in Honda et al, Analytical Biochem, 180, pp. 351–357 (1989).

The saccharide compound reacted with the 3-alkyl-5-pyrazolinone derivative, is generally stable; however, some reversibility of the derivatization reaction can be observed at room temperature, over time. Accordingly, the saccharide compound reacted with the 3-alkyl-5-pyrazolinone derivative is preferably analyzed by HPLC soon after the reaction, and in any event, the saccharide compound reacted with the 3-alkyl-5-pyrazolinone derivative is preferably stored at low temperature, preferably $\leq 10°$ C., more preferably at about 4° C.

After derivatization, the reaction mixture may be extracted with an organic solvent such as benzene, toluene, xylene, carbon tetrachloride, dichloromethane, chloroform, diethyl ether, dibutyl ether and hexane to remove PMP. The choice of extraction solvent is generally not critical; however, when analyzing neutral saccharide compounds, the solubility of the saccharide compounds in the extraction solvent may be of concern. Accordingly, when analyzing for neutral saccharide compounds, non-polar solvents such as benzene, toluene, xylene, dibutyl ether and hexane is preferred.

The aqueous layer may then be analyzed by HPLC methods on a reverse phase HPLC column. Any silica based support bearing hydrophobic groups, such as $C_4$, $C_8$, or $C_{18}$ hydrophobic groups may be used. A synthetic polymer support may also be used. Typical particle sizes are those suitable for analytical analysis, preferably from 5 to 20 $\mu$m.

Suitable reverse phase HPLC columns are $C_{18}$ columns.

A suitable solvent system is a two solvent system of 100 mM ammonium acetate buffer at pH 4.5 to $\leq 7.5$, preferably 5.5 with 10% and 25% acetonitrile, using a gradient elution program. Phosphate and carbonate based buffer systems are also possible.

The present invention also provides for a method of monitoring a disease state of a patient by analysis (quantitative, qualitative or both) of the oligosaccharide state of a patient's biological fluid. There is known correlation between the rate of urinary excretion of sialylated oligosaccharides and the clinical symptoms of rheumatoid arthritis (Maury et al, Annals of Rheumatic Diseases, 41, pp 268–271 (1982)), Systemic Lupus erythematosus (Maury et al Arthritis and Rheumatism, 24, pp 1137–1141 (1981)), myocardial infarction (Huttunen et al J. Molecular and Cellular Cardiology, 4, pp 59–70 (1972)) and pregnancy (Lemonnier et al Biomedicine, 24, pp 253–258 (1976)). Such a monitoring method comprises analyzing a biological fluid of a patient for the state of saccharide compound composition (qualitative, quantitative or both) and conducting further analysis of a patient's biological fluid at a later time. Changes in the saccharide compound composition of a biological fluid are indicative of a change in the physiological state of a patient and therefore such information can be correlated with the progress of a disease state. Accordingly, by monitoring changes in the concentration and type of oligosaccharides, the progress of a disease state can be monitored. The utility of such a method of monitoring, is that it provides a new method of analysis of the progress of a disease state.

The present invention also provides for a method of monitoring the saccharide composition state of a patient receiving oligosaccharides as a pharmaceutical therapy, by analysis (quantitative, qualitative or both) of the oligosaccharide state of a patient's biological fluid. Oligosaccharide compounds are being used for pharmaceutical therapy such as anti-adhesive therapy of bacterial infections and in the treatment of vascular reperfusion injury. Accordingly, the present analysis method provides a method of monitoring the fate of a saccharide compound which has been administered for a pharmaceutical therapy. The utility of such a method of monitoring is that it provides a method of monitoring the fate, and therefore the bioavailability of an oligosaccharide, in a patient receiving oligosaccharide pharmaceutical therapy.

Other features of the invention will become apparent in the course of the following descriptions of exemplary embodiments which are given for illustration of the invention and are not intended to be limiting thereof.

Equipment and Supplies

I. Beckman HPLC System Gold, equipped with System Gold Programmable Solvent Delivery Module 126 (S/N 090-2326), or equivalent II. Beckman System Gold Diode Array Detector Module 168 (S/N 271-2016), or equivalent III. Beckman System Gold Analog Interface Module 406 (S/N 473-3307), or equivalent IV. Beckman System Gold Autosampler Model 507 equipped with cooling system (S/N 474-1807), or equivalent V. Beckman Glass Buffer Containers (set of four, 1 L), or equivalent VI. Beckman System Gold Software, or equivalent VII. Recirculating Water Bath—Brinkman, Model Lauda RMS 6 (P/N N37015), equipped with a calibrated thermometer, or equivalent VIII. Speed-Vac Plus—Savant Instruments, Inc., Model SC110A-120 (S/N SC110A-4F260498-1H), or equivalent IX. Reacti-Therm Heating Module—Pierce Co., Model No. 18970, or equivalent X. Reacti-Block V-1—Pierce Co. (P/N 18819, Lot No. 95018819), or equivalent XI. Accumet pH Meter—Fisher Scientific, Model 50 (P/N 300035.1, S/N C0012074), or equivalent XII. Accumet pH Electrode—Fisher Scientific (P/N 13-620-291, S/N 4004076), or equivalent XIII. Autosampler Vials—Rainin Instrument Co., Inc. (P/N 54-1.1STVG), or equivalent XIV. CHO C-18 MPLC Cartridge—Applied Biosystems Division of Perkin Elmer Co., 5 micron, 220×2.1 mm (P/N 401660, S/N 185433), or equivalent XV. Ultrafree-MC Filter Cartridge—Millipore Co., NMWL of 10,000 (P/N UFC3TGC00), or equivalent XVI. Poly-Prep Chromatography Columns—Bio-Rad Laboratories (P/N. 731-1550), or equivalent XVII. Glass Vacuum Filtration System—Rainin Instrument Co., 47 mm in diameter (P/N 419380), or equivalent XVIII. Nylon Filtration Membrane—Fisher Scientific, 47 mm in diameter, 5 μm pore size (P/N N50SP04700), or equivalent XIX. pH Paper—Fisher Scientific, color pHast pH 0–14 (P/N 9590), or equivalent Samples and Reagents I. 3'-Sialyllactose—Produced by Neose Technologies, Inc., >99% pure, reference standard (Lot No. 1994RS02), or equivalent II. 6'-Sialyllactose—Produced by Neose Technologies, Inc., >99% pure, reference standard (Lot No. KP03-43-2), or equivalent III. Glacial Acetic Acid—Fisher Scientific Co. (P/N A34-212), or equivalent IV. Trifluoroacetic Acid—Aldrich Chemical Co., spectrophotometric grade, 99+% pure (P/N 30,203-1), or equivalent V. Pyridine—Sigma-Aldrich, HPLC grade, 99.9+% pure (P/N 27,040-7), or equivalent VI. Methanol—Fisher Scientific Co., Certified ACS grade (P/N A412-4), or equivalent VII. Chloroform—Fisher Scientific Co., Optima grade (P/N A297-4), or equivalent VIII. Hydrochloric Acid—Fisher Scientific Co., ACS reagent (P/N A144-212), or equivalent IX. Sodium Hydroxide—Sigma Chemical Co., ACS reagent (P/N S-0899), or equivalent X. 3-methyl-1-phenyl-2-pyrazolin-5-one (PMP)—Sigma Chemical Co., reagent grade (P/N M-5645), recrystalized in methanol before use (see below), or equivalent.

XI. Dowex 1-X8—Bio-Rad Laboratories, 200–400 mesh, acetate form (P/N 140-1453, Lot No. 49625A), or equivalent XII. Benzoic Acid—United States Pharmacopeia. Convention, Inc., Rockville, Md., USP reference standard (P/N 5500-2, Lot. No. F-3), or equivalent

EXAMPLE 1

Human blood plasma sample is first mixed with deionized (DI) water (plasma:water, 1.5:1, v/v) containing a known amount of 6'-sialyllactose Reference Standard. The mixture is then filtered through an Ultrafree-MC filter unit with Nominal Molecular Weight Limit (NMWL) of 10,000 to remove large molecules. The filtrate is then applied to a Dowex 1-X8 anion exchange column to purify and concentrate sialyloligosaccharides in plasma. After being dried on a Speed-Vac, the sample is labeled with a chromophore, 3-methyl-l-phenyl-2-pyrazolin-5-one (PMP), which is specific for reducing aldoses. The labeled sample is then analyzed by HPLC using a reverse phase column. The absolute amount of sialyloligosaccharide is determined by comparing its peak area in the sample to that of the internal Reference Standard 6'-sialyllactose.

Procedure for PMP Recrystallization 30 g of PMP is slowly added to 200 mL of methanol at 50° C. with stirring, until it completely dissolved. PMP is crystallized out of the methanol solution, then cooled over night at -5° C. to improve crystallization. Crystallized PMP can then be recovered from methanol by filtration, washed once with cold methanol through filtration, and then dried under vacuum on a lyophilizer.

Reagent and Buffer Preparation

I. Water—Degas deionized water at aspirator pressure for at least 30 minutes while stirring. Vacuum filter degassed water.

I. 2M Ammonium Acetate—154.16 g of ammonium acetate QS with DI water to 1 L.

II. 2M Acetic Acid—114.4 mL of glacial acetic acid QS with DI water to 1 L.

III. 1M Acetic Acid—57.2 mL of glacial acetic acid QS with DI water to 1 L.

IV. 0.5M Pyridine Acetate—403 mL of pyridine and 286 mL of glacial acetic acid QS with DI water to 1 L.

V. 2M Ammonium Acetate buffer, pH 5.5—800 mL of a 2M ammonium acetate solution is brought to pH 5.5 by slowly adding 2M acetic acid solution using a transferring pipette, while monitoring the pH of the solution continuously with a pH meter until it reaches pH 5.5. a) 1.5M Sodium Hydroxide—3.0 grams of sodium hydroxide pellets are dissolve in 50 mL of DI water.

VI. 0.5M Hydrochloric Acid—2.1 mL of concentrated hydrochloric acid QS with DI water to 50 mL.

VII. 0.5M PMP—87 mg of recrystallized PMP and 1 mL of methanol are vortexed until it is completely dissolved, in an Eppendorf tube. This reagent is prepared daily before use.

VIII. Buffer A—50 mL of 2M ammonium acetate buffer (pH 5.5) and 100 mL of acetonitrile QS with DI water to 1 L. Vacuum filter the buffer solution before use.

IX. Buffer B—50 mL of 2M ammonium acetate buffer (pH 5.5) and 250 mL of acetonitrile QS with DI water to 1 L. Vacuum filter the buffer solution before use.

X. Buffer C—900 mL of degassed DI water and 1 mL of trifluoroacetic acid QS with DI water to 1 L. Vacuum filter the solution before use.

XI. Buffer 900 mL of acetonitrile and 1 mL of trifluoroacetic acid QS with acetonitrile to 1 L. Vacuum filter the solution before use.

Sample Preparation

I. Transfer 750 μL of blood plasma to be analyzed to an Eppendorf tube.

II. Add 500 μL of DI water containing 3.0 μg/mL of 6'-sialyllactose and vortex well.

III. Transfer 800 μL of the above mixture into 2 Ultrafree-MC filter cartridges (400 μL each).

IV. Centrifuge the filter cartridges at 10,000 rpm for 3 hours in an Eppendorf Microcentrifuge.

V. Transfer 500 µL of the filtrate onto a Dowex 1-X8 column.

Ion Exchange Chromatography on Dowex 1-X8

VI. Pack a Poly-Prep Chromatography column with Dowex 1-X8 aqueous resin slurry to a final bed volume of 0.8 mL.

VII. Wash it sequentially with 4 mL of DI water, 4 mL of methanol, 4 mL of DI water, 4 mL of 1M acetic acid and 10 mL of DI water.

VIII. Load 0.5 mL of sample prepared above onto the top of the resin and let it flow through.

IX. Wash the column with 2 mL of DI water and discard eluant.

X. Wash the column with 0.5 mL of 0.5M pyridine acetate buffer, pH 5.0, and discard eluant.

XII. Elute the column with 1.0 mL of 0.5M pyridine acetate buffer, pH 5.0, and collect the eluant in a 1.5 mL Eppendorf tube.

XII. Evaporate the eluant to dryness at room temperature for 2 hours in a Speed-Vac.

PMP Derivatization Chemistry

I. Reconstitute the dried sample by adding 60 µL of DI water to the 1.5 mL Eppendorf tube and vortex well.

II. Add 75 µL of 0.5M PMP in methanol and 15 µL of 1.5M sodium hydroxide solution.

III. Vortex the reaction mixture and incubate it at 70° C. for 2 hours in a heating block.

IV. Add 50 µL of 0.5M hydrochloric acid and mix well.

V. Check with pH paper that the pH of the reaction is between 3–4 and adjust it if necessary with 0.5M hydrochloric acid solution.

V. Add 0.5 mL of chloroform and vortex for at least 5 seconds.

VI. Carefully remove the chloroform (bottom) layer with a 200 µL Micro-Pipette and discard it properly.

VII. Repeat steps 6 and 7 two more times.

VIII. Save the aqueous layer for analysis by HPLC.

HPLC Analysis

Eluants

I. Eluant A—100 mM ammonium acetate buffer, pH 5.5, with 10% acetonitrile

II. Eluant B—100 mM ammonium acetate buffer, pH 5.5, with 25% acetonitrile

III. Eluant C—DI water containing 0.1% trifluoroacetic acid

IV. Eluant D—Acetonitrile containing 0.1% trifluoroacetic acid

Method Conditions

I. Install the CHO C-18 column into the HPLC column holder and install this assembly in the Beckman System Gold HPLC system.

II. Set the flow rate to 200 µL/min and the wavelength to 245 nm on the UV detector.

III. Wash the column with 100% Buffer B for 1 hour (for new columns only).

IV. Equilibrate the column for 10 min with 35% Buffer A, 65% Buffer B.

V. For manual injection, carefully draw 50 µL of the sample with a syringe (not the chloroform at the bottom of the vial).

VI. For automatic injection with the Beckman Model 507 autosampler, set the circulating water bath coolant temperature to 4° C. with a calibrated thermometer.

VII. Transfer the samples to autosampler vials and program the autosampler to inject 50 µL each of the samples in Microliter Injection Mode.

VIII. HPLC system is operated at room temperature.

EXAMPLE 2 System Suitability

The system suitability test is conducted to ensure that the PMP derivatization chemistry and the chromatography conditions used enable separation of the analyte from other potential contaminants. In addition to 3'-sialyllactose (the analyte) 6'-sialyllactose (the internal standard), glucose (which occurs in blood), lactose and sialic acid (potential break-down products from 3'- and 6'-sialyllactoses) are analyzed.

Procedure 63.3 mg of 3'-sialyllactose and 6'-sialyllactose each, 34.2 mg of lactose, 309 mg of sialic acid and 18.0 mg of glucose are placed into a 100 mL volumetric flask QS with DI water to 100 mL. The final concentrations of 3'-sialyllactose, 6'-sialyllactose, lactose and glucose are 1.0 nmol/µL each.

Pipette 10 µL of the above sample and 50 µL of DI water into an Eppendorf tube. Derivatize the sample with PMP as described in PMP Derivatization Chemistry. Add 850 µL of DI water, and inject 50 µL of the sample into HPLC as described in HPLC Analysis. As the PMP derivatization chemistry is only specific for reducing aldoses, sialic acid, a break-down product of 3'- and 6'-sialyllactoses, will not be labeled. Sialic acid, therefore, will not be detected during HPLC analysis.

Results

TABLE 3

Results of System Suitability Study

| Sample | Ret. Time Col. (Min) | Efficiency (N) | Resolution (R) | Tailing Factor (T) |
|---|---|---|---|---|
| 6'-sialyllactose | 19.54 | 10892 | 5.11395 | 1.30431 |
| 3'-sialyllactose | 25.61 | 13349 | 1.64846 | 1.25140 |
| Lactose | 30.80 | 17574 | 5.70581 | 1.17808 |
| Glucose | 34.34 | 18668 | 3.66122 | 1.32572 |

EXAMPLE 3

Accuracy

Accuracy is the closeness of test results obtained by the method to the true value. Accuracy is determined by comparing assay values obtained for a test sample of established purity with the known quantities used to prepare the test solution.

Procedure 60.0 mg of 3'-sialyllactose and 6'-sialyllactose into a separate 1 L volumetric flask QS with DI water to 1 L. The final concentrations of 3'-sialyllactose and 6'-sialyllactose in each stock solution is 60 µg/mL. The 3'-sialyllactose stock solution is diluted with DI water to the following concentrations, 0.10 µg/mL, 0.30 µg/mL, 1.50 µg/mL, 3.0 µg/mL, 6.0 µg/mL and 12.0 µg/mL. The 6'-sialyllactose stock solution is diluted with DI water to 6.0 µg/mL.

Transfer 160 µL of 3'-sialyllactose solution at each concentration into a separate Eppendorf tube. Add 160 µL of 6.0 µg/mL 6'-sialyllactose solution and 480 µL of blood plasma to each Eppendorf tube. Transfer 160 µL of 3.0 µg/mL and 12.0 µg/mL 3'-sialyllactose solutions into a separate Eppendorf tube and label them as Unknown 1 and Unknown 2 respectively. Add 160 µL of 6.0 µg/mL 6'-sialyllactose solution and 480 µL of blood plasma to each Unknown Eppendorf tube. Vortex each tube well. Transfer the sample in each Eppendorf tube into two Ultrafree-MC filter cartridges (400 µL each) and centrifuge them as described in Sample Preparation. The filtrates from both filter cartridges for each sample are combined, and 500 µL is chromatographed on Dowex 1-X8 column, derivatized with PMP, and then analyzed in duplicate injections by HPLC as described above. The mean integrated peak area for duplicate injections of each sample is plotted vs. the corresponding serum concentration of 3'-sialyllactose (calculated based on a dilution factor of 3.0 from the procedure described above) to generate a standard curve. X is expressed as µg/mL. Y is expressed as mean integrated peak area. The concentrations of 3'-sialyllactose in Unknown 1 and Unknown 2 are calculated based on the integrated peak area of 6'-sialyllactose and the standard curve (using Beckman System software).

The percent recovery is calculated as actual concentration/theoretical concentration X 100.

Results

TABLE 7A

Standard Curve Data of 3'-SL Analysis in Serum (with 6'-SL as internal standard)

| Conc. in Serum (mg/mL) | Intg Inj#1 | Intg Inj#2 | Intg Avg | |
|---|---|---|---|---|
| 0.03333 | 0.11247 | 0.12094 | 0.11670 | 0.15624 |
| 0.10000 | 0.17106 | 0.17601 | 0.17354 | 0.19746 |
| 0.50000 | 0.43505 | 0.46239 | 0.44872 | 0.44479 |
| 1.00000 | 0.82595 | 0.85913 | 0.84254 | 0.75394 |
| 2.00000 | 1.35432 | 1.36080 | 1.35756 | 1.37226 |
| 4.00000 | 2.58889 | 2.60015 | 2.59452 | 2.60888 |
| Correlation coefficient | | | 0.99765 | |
| Slope | | | 0.61831 | |
| Intercept | | | 0.13563 | |

TABLE 7B

3'-SL Analysis in Unknowns (with 6'-SL as internal standard)

| | Unknown 1 | Unknown 2 |
|---|---|---|
| Theoretical Conc. (µm/mL) | 1.000 | 4.00 |
| Calculated Conc. (µm/mL) | 0.989 | 4.090 |
| % Recovery | 98.9% | 102.3% |

EXAMPLE 4

Sample Preparation for Urine

1) Transfer 200 µL of urine sample to be analyzed to each of two 10,000 NMWL Ultrafree-MC filter cartridges.

2) To one filter cartridge from step 1) above add 200 µL of D.I. water and to the other add 200 µL 6.0 µg/mL of 6'-sialyllactose and mix well.

Centrifuge the filter cartridges at 10,000 rpm for 20 minutes in an Eppendorf Microcentrifuge.

Anion Exchange Chromatography, PMP Derivatization and HPLC Analysis are carried out the same way as for the blood samples of Example 1.

Data Calculation and Analysis

1) The concentration of 3'-sialyllactose in urine is expressed as X. After 1:1 dilution with either D.I. water or internal reference standard solution 6'-sialyllactose, its concentration becomes X/2. After ultracentrifugation, the amount applied to the solid phase extraction cartridge is:

$$\frac{X}{2} * 300 = 150X$$

After the samples are PMP-labeled, the final volume of the reaction mixture is 150 µl, the concentration of 3'-sialyllactose during HPLC analysis is:

$$\frac{150X}{150} = X$$

Therefore, the concentration of 3'-sialyllactose during HPLC analysis is equivalent to that in urine. 2) For each urine sample, two parallel analyses are performed. In the first analysis, the urine sample is diluted 1:1 with D.I. water. In the second analysis, the urine sample is diluted 1:1 with an internal reference standard solution of 6'-sialyllactose (6 µg/ml). As both 6µ-sialyllactose and 3µ-sialyllactose are naturally present in human urine, the concentration of 3'-sialyllactose in urine can be calculated according to the ratios of 6'-sialyllactose and 3'-sialyllactose in both analyses and the amount of 6'-sialyllactose. Assume the concentration of 3'-sialyllactose is X in both water diluted sample and internal standard diluted sample, that of 6'-sialyllactose is Y in water diluted sample and Y+6 in internal standard diluted sample. The HPLC peak area is A for 3'-sialyllactose, B for 6'-sialyllactose in water diluted sample and C for 3'-sialyllactose, D for 6'-sialyllactose in internal standard diluted sample. The peak area is proportional to the concentration of the sample. Therefore, $$\frac{Y/2}{X/2} = \frac{Y}{X} = \frac{B}{A}$$

$$\frac{(Y+6)/2}{X/2} = \frac{Y+6}{X} = \frac{D}{C} \Rightarrow \frac{Y}{X} +$$

$$\frac{6}{X} \Rightarrow \frac{B}{A} + \frac{6}{X} = \frac{D}{C} \Rightarrow X = \frac{6}{D/C - B/A}.$$

System Suitability Results

| Sample | Retention time (min) |
|---|---|
| 6'-sialyl-N-acetyllactosamine (6'SLN) | 16.72 ± 5% |
| 6'-Sialyllactose (6'SL) | 18.43 ± 5% |

-continued

System Suitability Results

| Sample | Retention time (min) |
|---|---|
| 3'-sialyl-N-acetyllactosamine (3'SLN) | 23.49 ± 5% |
| 3'-Sialyllactase (3'SL) | 24.97 ± 5% |
| Lactose | 30.01 ± 5% |
| Glucose | 33.76 ± 5% |

Linearity Study of Human Urine spiked with 3'-Sialyllactose using a known amount of 6'-sialyllactose as internal standard

| Conc. 3'SL added ($\mu$g/mL) | 3'SL Intg Area Diluent | | 6'SL Intg Area Diluent | | ratio of 6' to 3'W | ratio of 6' to 3'S | Measured Conc. of 3'SL (ug/mL) |
|---|---|---|---|---|---|---|---|
| | W | S | W | S | | | |
| 0 | 24.2908 | 29.4265 | 4.81714 | 39.7214 | 0.1983 | 1.3499 | 5.2104 |
| 1 | 29.3498 | 31.5919 | 3.91508 | 34.7274 | 0.1334 | 1.0992 | 6.2121 |
| 5 | 47.0061 | 53.7618 | 3.64437 | 37.3388 | 0.0775 | 0.6945 | 9.7246 |
| 10 | 79.2044 | 76.4369 | 4.40161 | 36.9802 | 0.0556 | 0.4838 | 14.0112 |
| 20 | 121.707 | 130.602 | 3.82014 | 37.8314 | 0.0314 | 0.2897 | 23.2306 |
| 50 | 284.975 | 273.431 | 4.65246 | 37.6411 | 0.0163 | 0.1377 | 49.4494 |
| 100 | 590.799 | 577.802 | 4.74208 | 40.3071 | 0.0080 | 0.0698 | 97.1931 |

W = water
S = internal standard

| | 6'SL Intg Area | | | |
|---|---|---|---|---|
| | W | S | | |
| AVG | 4.28469 | 37.7925 | SL0PE | 0.9158363 |
| SD | 0.48374 | 1.84066 | INTCPT | 4.9551285 |
| RSD | 11.2900 | 4.87045 | RSQ | 0.99965 |

Water and the internal standard are diluents for the sample being analyzed for.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent: of the United States is:

1. A method for analyzing for reducing saccharide compounds in a biological fluid comprising charged reducing saccharide compounds and neutral reducing saccharide compounds, which comprises:

(i) filtering the biological fluid through a membrane or a filtration device, thereby obtaining a filtered biological fluid;

(ii) separating said charged reducing saccharide compounds from said neutral reducing saccharide compounds by contacting said filtered biological fluid with an anion exchange medium, thereby causing said charged reducing saccharide compounds to be retained on said anion exchange medium;

(iii) eluting said neutral reducing saccharide compounds from said anion exchange medium to provide a first eluate;

(iv) eluting said charged reducing saccharide compounds from said anion exchange medium to provide a second eluate;

(v) derivatizing said second eluate with a 3-alkyl-5-pyrazoline derivative of the formula

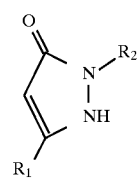

wherein $R_1$ is a $C_{1-12}$ alkyl group; and
$R_2$ is a $C_{1-12}$ alkyl group; a substituted $C_{1-12}$ alkyl group, wherein said substitutions are $C_{1-8}$ alkyl, $C_{1-8}$ alkoxy, or halogen; or a chromophore selected from the group consisting of phenyl, naphthyl, benzyl and pyridyl, wherein said chromophore is unsubstituted or substituted with $C_{1-8}$ alkyl, $C_{1-8}$ alkoxy or halogen;

(vi) extracting the derivatized eluate with an organic solvent to provide an aqueous phase and an organic phase; and (vii) analyzing said aqueous phase by HPLC analysis.

2. The method of claim 1 which further comprises:

(viii) derivatizing said first eluate with a 3-alkyl-5-pyrazoline derivative of the formula

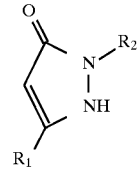

wherein $R_1$ is a $C_{1-12}$ alkyl group; and
$R_2$ is a $C_{1-12}$ alkyl group, a substituted $C_{1-12}$ alkyl group, wherein said substituents are $C_{1-8}$ alkyl, $C_{1-8}$ alkoxy, or halogen or a chromophore selected from the group consisting of phenyl, naphthyl, benzyl and pyridyl, wherein said chromophore is unsubstituted or substituted with a $C_{1-8}$ alkyl, $C_{1-8}$ alkoxy or halogen;

(ix) extracting the derivatized eluate with an organic solvent to provide an aqueous phase and an organic phase; and (x) analyzing said aqueous phase by HPLC analysis.

3. The method of claim 1 or 2 wherein $R_1$ is $CH_3$ and $R_2$ is phenyl.

4. The method of claim 1, wherein said reducing saccharide compounds are sialyl oligosaccharides.

5. The method of claim 4 wherein said sialyl oligosaccharides are selected from the group consisting of 3'sialyllactose, 6'sialyllactose, 3'sialyllactosamine, 6'sialyllactosamine and mixtures thereof.

6. The method of claim 1, wherein said biological fluid is selected from the group consisting of whole blood, blood plasma, serous effusions, cerebral spinal fluid, saliva, milk, tears, sweat, pancreatic juice, gastric juice, sputum, pus, aqueous and vitreous humors from the eye, joint fluids and urine.

7. The method of claim 1, wherein said membrane or filtration device has a 10,000 to 50,000 Mw cut-off.

8. The method of claim 1, wherein said organic solvent is selected from the group consisting of benzene, toluene, xylene, carbon tetrachloride, dichloromethane, chloroform, diethyl ether, dibutyl ether and hexane.

9. The method of claim 1 wherein the biological fluid is obtained from a patient in need of monitoring for the progress of a disease state.

10. The method of claim 1 wherein the biological fluid is obtained from a patient receiving oligosaccharide therapy.

* * * * *